Feb. 20, 1973 L. H. SHOESMITH Plant Pat. 3,309
CHRYSANTHEMUM PLANT
Filed June 4, 1971
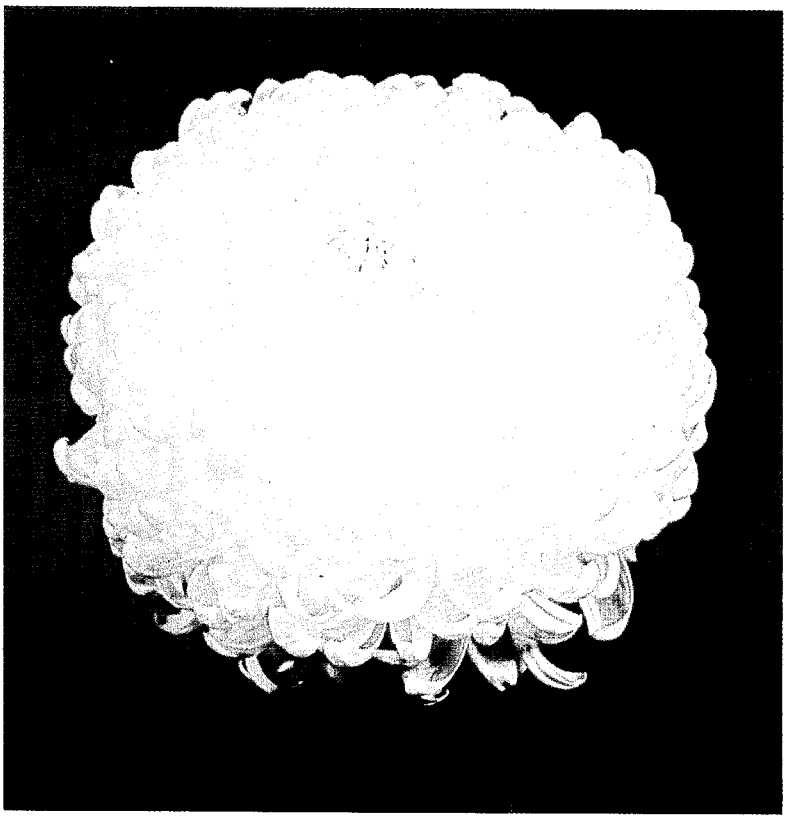
FIG. 1
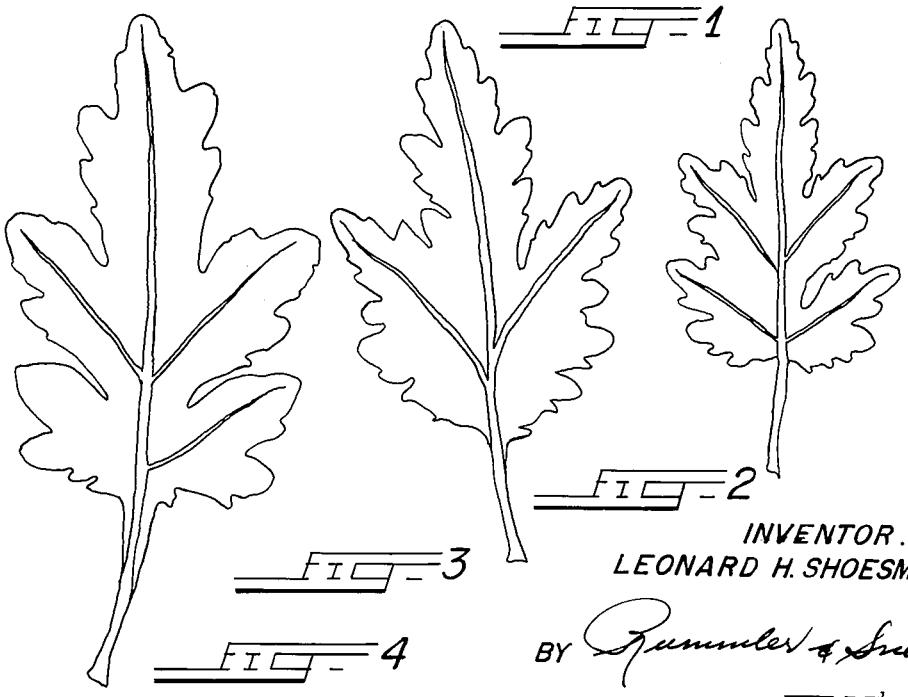
FIG. 2
FIG. 3
FIG. 4
INVENTOR.
LEONARD H. SHOESMITH
BY Rummler & Snow
ATTYS.

United States Patent Office

Plant Pat. 3,309
Patented Feb. 20, 1973

3,309

CHRYSANTHEMUM PLANT

Leonard H. Shoesmith, Westfield-Woking Surrey, England, assignor to Pan-American Plant Company, Chicago, Ill.

Filed June 4, 1971, Ser. No. 150,247
Int. Cl. A01h 5/00
U.S. Cl. Plt.—77 1 Claim

ABSTRACT OF THE DISCLOSURE

A new variety of chrysanthemum plant having a standard incurved type of bloom of very large size and pure white color, with no undertones of other colors, and being photoperiodic responsive for year-around flowering. The new plant has a very vigorous growth and is particularly distinguished from other varieties by its capability of producing a very large and full sized flower on a reduced amount of growing time.

BACKGROUND OF THE NEW PLANT

This new chrysanthemum plant was discovered by me in November 1968 at West Chicago, Ill., and was selected, as a seedling, from among many random crosses which were made during the course of extensive breeding efforts carried on by me with the object of producing new varieties having more vigorous growth habits and yet producing high quality flowers.

This new plant was selected for trial because of the unusually pure white color of its blooms and its apparently vigorous growth, and subsequent asexual reproduction of this plant under my direction at West Chicago, Ill., by means of cuttings, has shown the new plant to be the easy and very vigorous grower it was expected to be and also to have the capability of producing very large blossoms of the same pure white color of the original plant. It was also found that the new plant had a consistent ten-week response, for year-around flowering, under photoperiodic culture procedures.

Asexual propagation of this new plant, through successive generations at West Chicago, Ill., has shown the unusual white coloring of its blossoms and its easy and vigorous growth characteristics to be firmly fixed and to hold true from generation to generation.

DESCRIPTION OF THE DRAWINGS

This new variety of chrysanthemum plant is illustrated by the accompanying drawing in which the photographic figure shows the form of the blossom and its color characteristic, as nearly true as it is reasonably possible to obtain by conventional photographic procedures, and the ink drawn figures show the distinguishing configuration and relative sizes of the young, mid-aged and mature leaves of the new plant, shown from left-to-right respectively.

DESCRIPTION OF THE NEW PLANT

The following is a detailed description of my new variety of chrysanthemum plant, the color designations by code being according to the Horticultural Colour Chart of the Royal Horticultural Society of London, England (R. F. Wilson).

*The plant*

Origin: Seedling selected from random crosses.
Parentage: Unknown.
Classification:
*Botanic.*—*Chrysanthemum morifolium.*
*Commercial.*—Standard incurved.
Form: Perennial herbaceous bush.
Height: Two to four feet.

Growth: Vigorous, sturdy and upright, with good strength and normally branching.
Foliage: Quantity—abundant, 30 leaves per 3 feet of stem.
*Leaf size.*—Mature leaf—5½ inches long by 3½ inches wide.
*Shape.*—Ovate and culminate, generally culminate and serrated.
*Texture.*—Leathery and slightly glossy.
*Color.*—Upper side—Spinach Green 0960. Under side—Lettuce Green 861.
*Petioles.*—1⅛ inches long.
*Rachis.*—Pinnately.

*The bud*

Form: Oval from side view, round from top view.
Diameter: ⅝ inch—just before sepals separate.
Depth: ⅜ inch—just before sepals separate.
Opening: Bud opens slowly. Sepals begin to divide about 2 weeks from time bud becomes visible, flowering occurs about 4 weeks later.
Color: When sepals first divide and begin to unfurl—Scheeles Green 860/1.
Sepals: Polysepalous and hooded over bud. Spear-shaped and curl back as petals become fully developed.
Color:
*Inside.*—Scheeles Green 860/3.
*Outside.*—Scheeles Green 860/1.
Calyx:
*Shape.*—Round and flat. Does not split.
*Aspect.*—Slightly hairy.
Peduncle: Erect; diameter—¼ inch; length—½ inch; and slightly tomentose.
Color: Scheeles Green 860/1.

*The flower*

Blooming period: Photoperiod responsive for year-around flowering, with 10-week response.
Size: Very large. Diameter—6½ inches. Depth—5 inches.
Borne: Naturally raceme; singly when disbudded.
Shape: Flat and round. Becomes globular as petals develop.
Petalage: Petals are numerous with capitulum arrangement.
Form: Linear, with obtuse apex.
Color:
*Outer petals.*—White with base of Chartreuse Green 663.
*Inside petals and reverse side of petals.*—Very pure white with no undertones of other colors.
Texture: Medium soft. Appearance: Velvety.
Petaloids: None.
Peduncle: Sturdy, erect and upright, ½ inch long.
Color: Scheeles Green 860/3.
Effect of weather: Petals of flower become softer.
Persistence: Petals hang on and dry.
Fragrance: None.
Lasting quality: 21 days on the plant; 14 days as a cut flower.

*Reproductive organs*

Stamens: 5 syngenesious stamens, connate by their anthers to form a cylinder about the style.
Filaments: ¼ inch long. Light Yellow in color.
Pollen: Yellow.
Pistils: One for each ray floret, 3/16 inch long.
Stigmas: Yellow in color.
Ovaries: Inferior and bicarpellate.

This new variety of chrysanthemum plant is particularly distinguished from other varieties in that it is a very vigorous grower which permits a reduction in the amount of growing time normal to greenhouse culture of chrysanthemum plants, yet producing a full-sized flower. The new plant produces a very large white flower with medium-firm petals having a yellowish-green color when opening and turning to pure white when the flower reaches the full opened state. The plant appears to have its best growth when grown during the spring, summer and fall, or during high intensity sunlight periods.

I claim:

1. The new and distinct variety of chrysanthemum plant of the incurved type, substantially as herein shown and described, characterized by the substantially pure white color of its very large ball-shaped blooms; the very vigorous growth of the plant with a ten-week response under photoperiodic culture; and the long lasting characteristic of the blooms as cut flowers.

No references cited.

ROBERT E. BAGWILL, Primary Examiner